United States Patent [19]

Korpman

[11] Patent Number: 4,554,191

[45] Date of Patent: Nov. 19, 1985

[54] ETHYLENE-CONTAINING POLYMER FOAM/ADHESIVE SYSTEM

[75] Inventor: Ralf Korpman, Bridgewater, N.J.

[73] Assignee: Personal Products Company, Milltown, N.J.

[21] Appl. No.: 701,061

[22] Filed: Feb. 13, 1985

Related U.S. Application Data

[63] Continuation-in-part of Ser. No. 637,450, Aug. 3, 1984, abandoned.

[51] Int. Cl.[4] .............................. B32B 1/00; B32B 3/14
[52] U.S. Cl. ........................................ 428/35; 428/40;
428/77; 428/317.1; 428/354; 428/355; 604/387;
604/389
[58] Field of Search ................... 428/35, 40, 77, 78,
428/317.1, 317.3, 317.7, 354, 355; 604/387, 389

[56] References Cited

U.S. PATENT DOCUMENTS

| 3,575,175 | 4/1971 | McGuire | 604/387 |
| 3,643,662 | 2/1972 | McGuire et al. | 604/387 |
| 4,018,225 | 4/1977 | Elmi | 604/369 |
| 4,055,184 | 10/1977 | Karami | 604/369 |
| 4,358,489 | 11/1982 | Green | 428/317.7 |
| 4,377,614 | 3/1983 | Alfter et al. | 428/319.7 |

OTHER PUBLICATIONS

Volara Properties, Voltek-A Sekisui Co., (1/1980) 4 pp.
Closed Cell Foam Properties, Voltek-A Sekisui Co. (no date), 4 pp.
Versatility in Polyethylene Foams, Voltek-A Sekisui Co. (no date) 4 pp.

Primary Examiner—William J. Van Balen
Attorney, Agent, or Firm—Leonard Kean

[57] ABSTRACT

The invention provides a liquid-impermeable ethylene-containing polymer foam backing for an absorbent product adapted to be removably attached to a nether garment, there being adhesive attachment means positioned on the bottom surface of said backing for adhering said backing to the crotch portion of a nether garment. The preferred backing comprises a flexible shell, adapted to contain within it an absorbent structure.

18 Claims, 3 Drawing Figures

ETHYLENE-CONTAINING POLYMER FOAM/ADHESIVE SYSTEM

This application is a continuation-in-part of application Ser. No. 637,450, filed Aug. 3, 1984, now abandoned.

This invention relates to a liquid-impermeable ethylene-containing polymer foam backing for an absorbent product adapted to be removably attached to a nether garment, there being adhesive attachment means positioned on the bottom surface of said backing for adhering said backing to the crotch portion of said nether garment. The preferred backing comprises a flexible shell, adapted to contain within it, an absorbent structure.

The expression "ethylene-containing polymer foam" used herein signifies polyethylene homopolymers and ethylene-containing copolymers, preferably containing a major amount (by weight) of ethylene. For the optimum properties of the foam backing, it is preferred that the polymer be cross-linked, as by electron beam radiation. Preferred comonomers include vinyl acetate, acrylic and methacrylic acids and esters such as ethylene acrylate. Blends of such polymers can also be used.

BACKGROUND OF THE INVENTION

Many attempts have been made to provide absorbent products, such as disposable diapers, sanitary napkins, and incontinent pads which are used to absorb and to contain body fluids. Most of such products contain an absorbent batt which is placed between a liquid-impermeable backing and a liquid-permeable facing. In both the infant diaper and adult incontinent product marketplace, a product is needed which has a large storage capacity. In this connection, copending U.S. patent applications Ser. Nos. 535,193 and 626,167 disclose a disposable pad which comprises a liquid-impermeable, substantially flexible shell preferably thermoformed from an ethylene-containing polymer foam, said shell containing a superstructure capable of maintaining void volume when wet and an absorbent medium. The shell generally has a boat-like shape and ranges in thickness from about 1/64 inch to about $\frac{1}{4}$ inch. The shell has a length which ranges from about 4 inches to about 12 inches, a width measured from one rim to another across the top space from about 2 inches to about 7 inches, and a depth measured from a line extending across the width of the upper shell rim in the central portion from about 0.125 to about 2.5 inches. Adhesive lines are applied on the underside of the shell to provide the securement means for securing the pad to the clothing of the user. These adhesive lines are covered with release strips which when peeled from the adhesive strips leave the adhesive tacky.

Polyethylene film is a well known release surface for pressure sensitive adhesives, and thus it is clear that an extremely aggressive adhesive is necessary in order to provide a strong adhesion level to polyethylene film. It is even more difficult to obtain a strong adhesion level to polyethylene-containing foams. A common practice is to transfer coat a non-supported pressure-sensitive adhesive on a silicone liner to polyethylene film. When it was attempted to carry out a similar procedure in order to transfer coat a non-supported pressure-sensitive adhesive to polyethylene-containing foam, the resultant adhesive bond completely failed.

It must also be borne in mind that adhesive in a hot-melt state cannot be applied to foam in view of the fact that the foam is far too heat sensitive. Therefore, the desirable pressure-sensitive adhesive must be applied in the cold state. It is also impractical to use solvents for applying the adhesives, since massive ovens would be needed for removing the solvents. Many attempts have been made at improving the pressure-sensitive adhesive anchorage to ethylene-containing polymer foams via Corona or Flame treatment of the foam as well as by using various primers to enhance the bond, but none of these approaches has been completely adequate.

Surprisingly, it was found that when an adhesive of the same formulation as above, was coated on a reinforcing inner substrate having a non-recoverable extensibility of less than 100%, then said adhesive performed well on the foam backing.

In accordance with a preferred embodiment of the present invention, a thermoplastic rubber adhesive which is highly loaded with solid tackifying resin provides the desired bond to an ethylene-containing polymer foam surface, even without Corona, Flame or primer treatment. Said adhesive provides an adhesion to steel exceeding 120 oz/inch width.

It has been attempted, in the past, to utilize "double-faced" pressure-sensitive adhesive tape for securing a polyethylene film backing to the clothing of the user. Such double-faced tape consists of a thin, film-like substrate having adhesive coatings applied to each surface. When "standard" double-faced tapes are utilized for adhering to an ethylene-containing polymer foam backing, such tapes fail to satisfactorily perform their intended function. When the release strip is removed, it has the effect of delaminating the foam backing or pulling the adhesive completely away from the foam, rather than being cleanly released. This problem is overcome, in accordance with the present invention. Of course, the adhesive level of the double-faced tape attached to the undergarment must desirably be less than the adhesive level of the side of the double-faced tape attached to the ethylene-containing polymer foam backing, so as to permit the easy removal of the backing from the undergarment. This can be accomplished, either by reducing the adhesive level of the side of the double-faced tape attached to the undergarment, as compared to the opposite face of the tape, or, if the formulation of the adhesive is the same on both sides of the double-faced tape, then the adhesive level of one side may be reduced by covering part of the adhesive on said one side with a strip of non-adhesive material, or by omitting part of the adhesive on said one side.

THE PRIOR ART

The McGuire et al. U.S. Pat. No. 3,643,662 (as well as a related U.S. Pat. No. 3,575,175) describes a removable protective liner for nether garments which is temporarily, but securely, held to the interior crotch portion of nether garments by a narrow, double-faced, pressure-sensitive adhesive tape attached to the under surface of the liner. The adhesive tape possesses differential adhesion levels such that the adhesive layer that secures the tape to the protective liner possesses a greater level of adhesion so as to permanently adhere the tape thereto, than does the adhesive layer of the tape that temporarily, but securely, adheres the tape and the liner to the crotch portion of the nether garment. Although McGuire discloses the fact that the liner may be polyethylene film, there is no disclosure of any backing comprising ethylene-containing polymer foam and thus there is no teaching in McGuire concerning the necessity of providing an adhesive level sufficiently high so that the double-faced tape may be securely attached to a foam backing. Thus, in accordance with the present invention, the adhesive layer attached to the foam backing must have an adhesion to steel exceeding 120 oz/inch width, whereas in accordance with the McGuire patent the maximum adhesion of the adhesive layer of the face of the tape attached to the liner is 112 oz/inch width. It has also been discovered, in accordance with the present invention, that in order for the invention to be effective, the double-faced tape must be reinforced with an inner substrate that has a non-recoverable extensibility of less than 100%. Although McGuire discloses substrates which fall within this definition, nevertheless, there is no awareness of the criticality thereof since adhesion to the polyethylene film shown in McGuire presents far less difficulty than adhesion to ethylene-containing polymer foam in accordance with the present invention.

SUMMARY OF THE INVENTION

The present invention relates to a liquid-impermeable ethylene-containing polymer foam backing for an absorbent product adapted to be removably attached to a nether garment, said backing having top and bottom surfaces, there being adhesive attachment means positioned on the bottom surface of said backing, for temporarily, but securely, adhering said backing to the crotch portion of a nether garment, said attachment means comprising a double-faced, pressure-sensitive adhesive tape, said tape having a first face permanently adhered to said backing, and an opposite second face adapted to be temporarily attached to a nether garment, said first face of said tape having an adhesion to steel exceeding 120 oz/inch width, with said second face of said tape having an adhesion to steel exceeding 75 oz/inch width, said tape being reinforced with an inner substrate having a non-recoverable extensibility of less than 100%.

In accordance with a preferred embodiment of the present invention, the backing is thermoformed in the form of a substantially flexible shell having a depth of at least about ⅛ inch, said shell having an inner inside surface and an outside bottom surface, said shell being adapted to contain within it an absorbent structure, said adhesive attachment means being positioned on said outside bottom surface of said shell. The shell is formed from a moldable substance which is liquid-impermeable. For example, the shell may be a polyethylene foam shell which is formed from a blown polyethylene foam sheet, subsequently subjected to molding by a thermal process. The shell generally has a boat-like shape and ranges from about 1/64 inch to about ¼ inch in thickness. The shell has a length which ranges from about 4 inches to about 12 inches, a width measured from one rim to another across the top space from about 2 inches to about 7 inches, and a depth measured from a line extending across the width at the upper shell rim in the central portion from about ⅛ inch to about 2.5 inches. The shell is adapted to have placed therein an absorbent superstructure which substantially fills the shell, is at least slightly compressible and is capable of maintaining a liquid void volume even when wet. The superstructure may be comprised of a fibrous web, a foam, entangled resilient fibers or mixtures thereof. The absorbent medium may comprise superabsorbent material, hydrophilic fibers which are loosely compacted or formed into a nonwoven web, wadding, tissue, peat moss, mixtures thereof or the like.

It should be noted that the second face of the adhesive tape is normally covered with a release strip. When the absorbent product is ready for use, the release strip is peeled away leaving the adhesive on the second face of the tape still tacky so that it can be applied to the undergarment.

In the instance wherein the adhesive formulation is common to both the first and second faces of the tape, then it is necessary for the first face of the tape to be provided with a greater surface area of adhesive than that of the second face. In this manner, the adhesion to the foam backing will be much greater than that of the adhesion to the undergarment. The surface area of the layer of adhesive on the second face of the tape may be reduced by covering a portion of said second face with a non-adhesive strip of material. Alternatively, a portion of the substrate to which the second face of the adhesive is applied can be left bare (as for instance leaving a central bare strip in the middle of the second face of the tape).

When the backing comprises an ethylene-containing polymer foam shell, said shell preferably has a thickness of from 1/64 inch to about ¼ inch. The depth of the shell measured from a line extending across the width at the upper shell rim in the central portion is preferably from about ⅛ inch to about 2½ inches.

The adhesive used in the double-faced tape of the present invention is preferably one of those based on A-B-A block copolymers. Such adhesives such as shown in U.S. Pat. Nos. 4,136,071 and 3,676,202 can be rendered highly tacky by mixing certain A-B block copolymers with certain A-B-A block copolymers with a high proportion of solid tackifying resin. The same desirable adhesive can also be produced by using styrene-isoprene-styrene polymer which is polymerized to the correct A-B block, A-B-A block ratio as is the case with Kraton 1117 (which is a thermoplastic elastomeric A-B-A block copolymer sold by the Shell Chemical Company). The A-B-A copolymer may be tackified with a high loading of various solid resins like hydrocarbon, polyterpene or rosin esters, (there being more than 100 parts of resin by weight to 100 parts of elastomer). The formulation in question can be coated onto the substrate by hot melt, calendar, or solvent methods. Both the first and second faces of the double-faced adhesive tape are preferably coated with an adhesive layer comprising a thermoplastic elastomeric component and a resin component, said thermoplastic elastomeric component consisting essentially of about 10 to 75 parts of a simple A-B block copolymer wherein the A blocks are derived from styrene or styrene homologues and the B blocks are derived from isoprene and about 90 to 25 parts of an A-B-A block copolymer, wherein the A and B blocks are as defined above, the A blocks in the A-B block copolymer constituting about 10 to 35% by weight of the A-B copolymer and the total A-B and A-B-A copolymers comprising not above about 30% styrene. The above formulation preferably includes about 100 to 175 parts (and more preferably, about 120 to 140 parts) of a solid tackifier, all of said parts being parts per 100 parts by weight of the thermoplastic elastomeric component, when the formulation is to be coated on the first face of the double-faced adhesive tape. When the formulation is to be coated on the second face of the adhesive tape, then the resin component preferably consists essentially of about 60 to 120 parts of a solid tackifier.

For both the first and second faces of the adhesive tape, the adhesive layer preferably comprises about 25 to 45 parts of the A-B copolymer and about 75 to 55 parts of the A-B-A copolymer, per 100 parts by weight of the thermoplastic elastomeric component.

The adhesive on the first face of the adhesive tape preferably comprises about 120 to 140 (and most preferably 120) parts by weight of a solid tackifier resin, per 100 parts by weight of the thermoplastic elastomeric component.

It should be noted that when the backing comprises a foam shell, the reinforcing inner substrate of the adhesive attachment means provides additional stability to the total foam structure.

The adhesive on the second face of the adhesive tape preferably includes about 85 to 95 (and most preferably 90) parts by weight of a solid tackifier resin, per 100 parts by weight of the thermoplastic elastomeric component.

U.S. Pat. Nos. 3,239,478 2,376,202 provide a good description of the elastomeric block copolymers utilized in the present invention.

The central reinforcing substrate utilized in the double-faced adhesive tape of the present invention preferably comprises plastic films, nonwoven fabrics, woven fabrics or paper.

In accordance with one embodiment of the present invention, the adhesive in both the first and second faces of the adhesive tape consists of a common formulation and the reinforcing substrate comprises a scrim or netting which is positioned closer to the second face of the tape than it is to the first face of the tape. The presence of the scrim or netting close to the surface of the second face of the tape acts to reduce the adhesive level of the second face and thus to bring about a differential in the adhesive level between the first and second faces.

In the instance wherein the central reinforcing substrate comprises an impervious film, then the adhesive layer of the first face and the adhesive layer of the second face of the tape must necessarily comprise different formulations (unless the surface area of the adhesive on the second face of the tape is reduced by covering said second face with a strip of non-adhesive material or by reducing the amount of adhesive on the second face).

Although any ethylene-containing polymer foam material can be utilized for preparing the foam shell of the present invention, nevertheless the preferred material is an ethylene/vinyl acetate copolymer.

Methods for preparing ethylene-containing polymer foams suitable for the backing of the present invention are disclosed in U.S. Pat. Nos. 4,213,925; 4,203,815; 3,959,189 and 4,252,906.

DETAILED DESCRIPTION OF THE INVENTION

Figure 1:
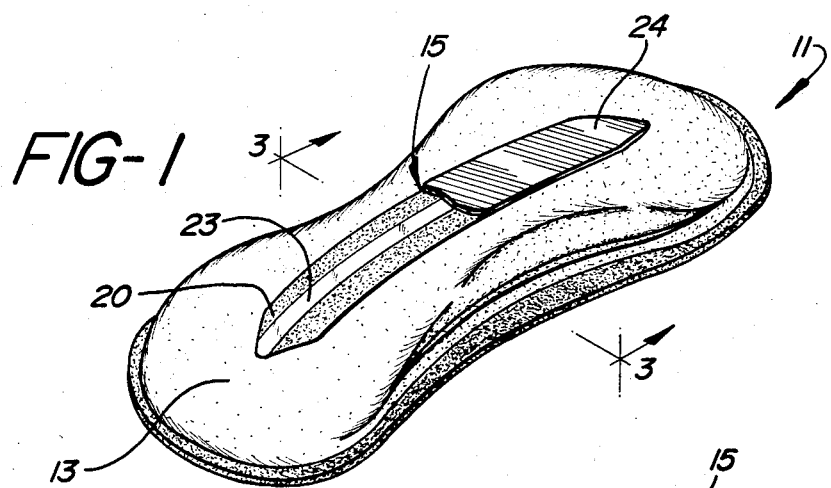
FIG. 1 depicts a bottom perspective view of the polyethylene-containing shell of one embodiment of the present invention.
Figure 2:
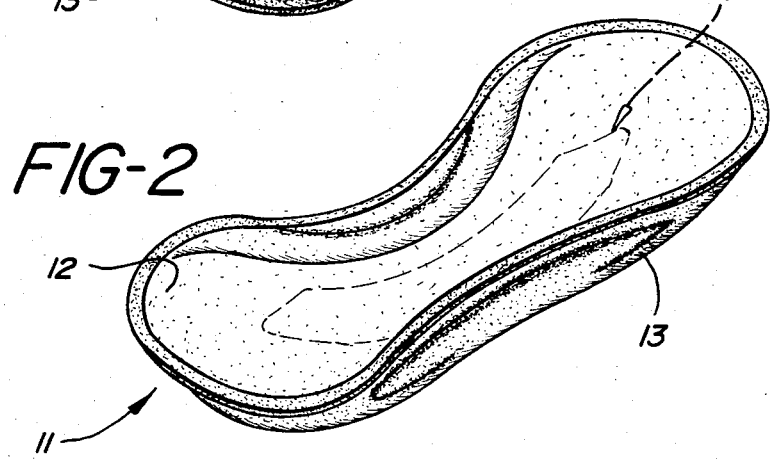
FIG. 2 depicts a top perspective view of the shell shown in FIG. 1.

FIG. 1 depicts a bottom perspective view of a liquid-impermeable ethylene-containing polymer foam backing for an absorbent product (in this instance a urinary pad), the backing consisting of a thermoformed shell 11 in the form of a boat. The shell 11 is adapted to contain an absorbent structure, not shown in the drawings. The bottom outside surface of the shell 11 is indicated at 13. FIG. 2 is a top perspective view of the shell 11, the interior portion of the shell being designated as 12.

As will be seen from FIG. 1, on the under surface of the shell 11 is a longitudinally extending, narrow adhesive attachment means 15. The adhesive attachment means 15 is a double-faced adhesive tape extending along a major part of the length of shell 11. As will be seen from FIG. 3 which is a cross-sectional view taken through lines 3—3 of FIG. 1, the attachment means 15 consists of a thin filmlike substrate 21 having a first adhesive coating 22 on one surface thereof and a second adhesive coating 20 on the other surface thereof. The substrate 21 may consist of any material which has a non-recoverable extensibility of less than 100%. Thus, the substrate may comprise plastic films, nonwoven fabrics, woven fabrics or paper. However, the preferred substrate is a 1 mil polyester plastic film.

The adhesive coating 22 has the following formulation (A):

Kraton 1117 (a polystyrene-polyisoprene-polystyrene structure sold by the Shell Oil Company): 100 parts
(Kraton 1117 is believed to comprise about 35 parts A-B and 65 parts A-B-A)
Wingtack 95: 120 parts
(Wingtack 95 is a solid tackifier resin consisting predominantly of polymerized structures derived from piperylene and isoprene sold by Goodyear Tire and Rubber Company. It has a softening point of about 95° C.)
Butyl Zimate: 2 parts
(Trademark for zinc di-n-butyldithiocarbamate, an antioxidant)
Santovar A: 1 part
(Trademark for 2,5-di-tert-amylhydroquinone, an antioxidant).

Figure 3:
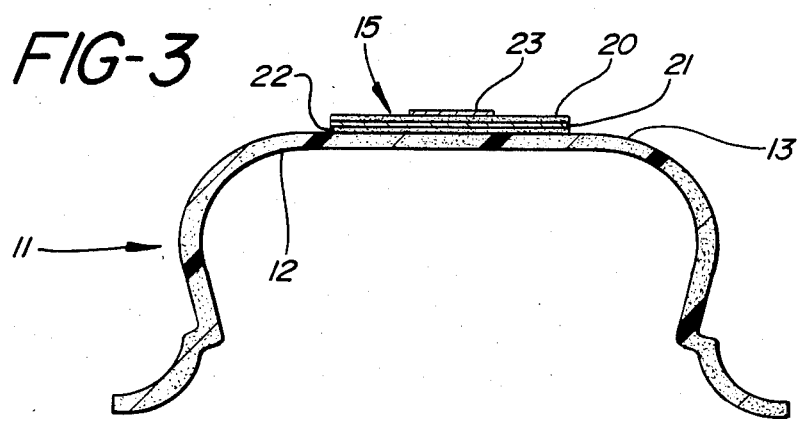
FIG. 3 is a cross-sectional view taken through lines 3—3 of FIG. 1.

The adhesive formulation 20, as shown in FIG. 3 is the same as that of adhesive formulation 22. However, in order to reduce the adhesive level of the second face 20 of the adhesive tape 15 a non-adhesive strip 23 of polyester is placed on layer 20.

The adhesive coating 22 is a pressure-sensitive adhesive which secures the narrow tape substrate 21 to the bottom surface of the shell 11 and the adhesive coating 20 is another pressure-sensitive adhesive coated on the outside surface of the substrate 21 and is protected by a release strip 24 (shown partly broken away at one end in FIG. 1). The release strip can be of any suitable film-like material that does not adhere too tenaciously to the adhesive coating 20 and particularly suitable is a semi-bleached Kraft paper one side of which has been silicone coated to provide for easy release of the paper strip 24 from the outer adhesive layer 20. The release strip 24 can be grasped by the fingers and readily lifted and peeled back from the surface of the adhesive layer 20 when it is desired to secure the shell 11 in the crotch portion of a nether garment.

To assure permanent attachment of the tape 15 to the foam shell 11 while at the same time assuring temporary, but secure, attachment of the tape 15 to the variety of fabrics from which nether garments are made, it is essential that the adhesive layer 22 and the adhesive layer 20 possess a differential level of adhesion. A differential level of adhesion is obtained when the opposite sides of the double-faced, pressure-sensitive adhesive tape 15 have a different adhesion level when the sides thereof are individually pressed into contact with the same surface material. The adhesion level is defined as that force required to strip or peel away a double-faced, pressure-sensitive adhesive tape which has been secured by one of its adhesive faces to the surface of a stainless steel plate and is quantified as oz/inches of width of the tape. The differential level of adhesion required by the double-faced, pressure-sensitive adhesive tape 15 used in accordance with the present invention is such that the adhesive layer 22 has a level of adhesion, as above defined, exceeding 120 oz/inch width, and preferably about 140 oz/inches width, and adhesive layer 20 has a level of adhesion exceeding 75 oz/width (and preferably about 100 oz/inch width). The ratio between the higher adhesion level of adhesive layer 22 and the lower adhesion level of adhesive layer 20 in any given double-faced, pressure-sensitive adhesive tape 15 is preferably about 1.4:1.

The liquid-impermeable substantially flexible shell 11 is formed from a moldable ethylene-containing polymer foam. The substance, when molded, provides a liquid-impermeable substantially flexible shell with a thickness ranging from about 1/64 inch to about ¼ inch. The shell, when deformed, substantially returns to its original shape. The polyethylene-containing foam shell is prepared by known thermal molding processing. The preferred formulation for forming the ethylene-containing polymer foam material is identified as Volara Type E which is a cross-linked ethylene/vinyl acetate copolymer foam. Also suitable for the present invention is a material identified as Volara Type A which is a cross-linked polyethylene foam. The products are manufactured and sold by Voltek, Inc., Lawrence, Mass. Preferably, the formulation is prepared in sheet form and approximately ⅛ inch in thickness. The sheet is subjected to thermal molding at a temperature of about 260° F. to form the foam shell. The shell is boat-like in shape, but is not limited thereto. The following is an alternative formulation (B) useful for adhesive layer 22:
Kraton 1107—50 parts
(comprising 15 parts styrene-isoprene and 85 parts styrene-isoprene-styrene)
Natural rubber—50 parts
Piccolyte S115—130 parts
(A beta pinene tackifier resin with a melting point of 115° C.)
Butyl zimate—2 parts
Santovar A—1 part
In the instance wherein layers 22 and 20 of the double-faced tape are separated by an impermeable substrate 21, the following is a suitable formulation (C) for adhesive layer 20 for adhesion to undergarments:
Kraton 1107—100 parts
Wingtack 95—90 parts
Butyl zimate—2 parts
Santovar A—1 part
Examples for the preparation of the foam backing of the present invention are as follows. These examples are not intended to be limiting in any way and extensions and modifications thereof, without departure from the spirit and scope of the invention, will become apparent from these examples.

EXAMPLE 1

A soft, flexible shell is formed by thermoforming an ethylene/vinyl acetate copolymer foam sheet. The shell has a length of 8 inches, a width at the widest point of 4⅜ inches and a width at the central portion at its narrowest point of 3¾ inches. The shell is ⅞ inches deep at the center from a line extending across the center from the edge of each rim of the shell.

A double-faced adhesive tape is prepared by coating formulation A on either side of a strip of 1 mil polyester tape, at a coating weight of 1 oz/square yard of adhesive on each side. Thereafter, a narrower strip of non-adhesive polyester tape is placed on one side of said double-faced tape so as to reduce the adhesive level on said one side. The double-faced tape is ⅝ inch wide and a ¼ inch strip of non-adhesive polyester tape is placed longitudinally along the length of said one side of said tape, providing two separated adhesive strips on either side of said polyester tape. Thereafter, the opposite side of the double-faced tape is applied longitudinally to the outside bottom surface of the foam shell. The side of the double-faced tape adhering to the foam shell has an adhesive level of 140 oz/inch width; and the opposite side of the double-faced adhesive tape adapted to be attached to an undergarment has an adhesive level of 100 oz/inch width. The resultant foam backing is found to be quite suitable for its intended purpose, i.e., no delamination of the foam occurs when the release strip is removed or when the backing is removed from an undergarment, after use.

From the foregoing it will be observed that numerous variations and modifications may be effected without departing from the true spirit and scope of the novel concept of this invention.

I claim:

1. A liquid-impermeable ethylene-containing polymer foam backing for an absorbent product adapted to be removably attached to a nether garment, said backing having top and bottom surfaces, there being adhesive attachment means positioned on the bottom surface of said backing, for temporarily, but securely, adhering said backing to the crotch portion of a nether garment, said attachment means comprising a double-faced, pressure-sensitive adhesive tape, said tape having a first face permanently adhered to said backing, and an opposite second face adapted to be temporarily attached to a nether garment, said first face of said tape having an adhesion to steel exceeding 120 oz/inch width, with said second face of said tape having an adhesion to steel exceeding 75 oz/inch width, said tape being reinforced with an inner substrate having a non-recoverable extensibility of less than 100%.

2. A liquid-impermeable ethylene-containing polymer foam backing for an absorbent product adapted to be removably attached to a nether garment, said backing having top and bottom surfaces, there being adhesive attachment means positioned on the bottom surface of said backing, for temporarily, but securely, adhering said backing to the crotch portion of a nether garment, said attachment means comprising (a) a double-faced, pressure-sensitive adhesive tape, said tape having a first face permanently adhered to said backing, and an opposite second face adapted to be temporarily attached to a nether garment, said first face of said tape having an adhesion to steel exceeding 120 oz/inch width, with said second face of said tape having an adhesion to steel exceeding 75 oz/inch width, said tape being reinforced with an inner substrate having a non-recoverable extensibility of less than 100%, said backing being thermoformed in the form of a substantially flexible shell having a depth of at least about ⅛ inch, said shell having an inner inside surface and an outside bottom surface, said shell being adapted to contain within it an absorbent structure, said adhesive attachment means being positioned on said outside bottom surface of said shell.

3. The backing of claim 1, wherein the adhesive layer of said second face of said tape is protected by a removable release strip when said adhesive layer is not in use.

4. The backing of claim 1 wherein the adhesive layer of said first face of said tape is of greater surface area than the adhesive layer of said second face of said tape.

5. The backing of claim 2, wherein said shell is an ethylene-containing polymer foam shell having a thickness from 1/64 inch to about ¼ inch.

6. The backing of claim 2, wherein said shell has a depth from about 0.125 to about 1.5 inches.

7. The backing of claim 2 wherein said shell has a boatlike shape.

8. The backing of claim 1 wherein the adhesive layer of at least said first face of said tape comprises a thermoplastic rubber adhesive containing a high proportion of solid tackifying resin.

9. The backing of claim 8 wherein said adhesive layer of said first face of said tape comprises a thermoplastic elastomeric component and a resin component, said thermoplastic elastomeric component consisting essentially of about 10 to 75 parts of a simple A-B block copolymer wherein the A blocks are derived from styrene or styrene homologues and the B blocks are derived from isoprene, and about 90 to 25 parts of an A-B-A block copolymer, wherein the A and B blocks are as defined above, the A blocks in the A-B block copolymer constituting about 10 to 35 percent by weight of the A-B copolymer and the total A-B and A-B-A copolymers comprising not above about 30% styrene, said resin component consisting essentially of about 100 to 175 parts of a solid tackifier, all of said parts being parts per 100 parts by weight of the thermoplastic elastomeric component.

10. The backing of claim 9 wherein said adhesive layer of said first face of said tape comprises about 25 to 45 parts of the A-B copolymer and about 75 to 55 parts of the A-B-A copolymer, per 100 parts by weight of the thermoplastic elastomeric component.

11. The backing of claim 10 wherein said adhesive layer of said first face of said tape comprises about 120 to 140 parts by weight of a solid tackifier resin, per 100 parts by weight of the thermoplastic elastomeric component.

12. The backing of claim 1 wherein said adhesive layer of said second face of said tape comprises a thermoplastic elastomeric component and a resin component, said thermoplastic elastomeric component consisting essentially of about 10 to 75 parts of a simple A-B block copolymer wherein the A blocks are derived from styrene or styrene homologues and the B blocks are derived from isoprene, and about 90 to 25 parts of a linear or radial A-B-A block copolymer, wherein the A and B blocks are as defined above, the A blocks in the A-B block copolymer constituting about 10 to 35 percent by weight of the A-B copolymer and the total A-B and A-B-A copolymers comprising not about 30% styrene, said resin component consisting essentially of about 60 to 120 parts of a solid tackifier, all of said parts being parts per 100 parts by weight of the thermoplastic elastomeric component.

13. The backing of claim 9 wherein said adhesive layer of said second face of said tape comprises about 25 to 45 parts of the A-B copolymer and about 75 to 55 parts of the A-B-A copolymer, per 100 parts by weight of the thermoplastic elastomeric component.

14. The backing of claim 13 wherein said adhesive layer of said second face of said tape comprises about 85 to 95 parts by weight of a solid tackifier resin, per 100 parts by weight of the thermoplastic elastomeric component.

15. The backing of claim 1, wherein the reinforcing substrate comprises plastic films, nonwoven fabrics, woven fabrics or paper.

16. The backing of claim 1, wherein the reinforcing substrate comprises a scrim or netting which is positioned closer to said second face of said tape than it is to said first face of said tape, the adhesive in both said first and second faces of said tape consisting of a common formulation.

17. The backing of claim 1, wherein the adhesive layer of said first face and the adhesive layer of said second face of said tape comprise different formulations and are separated from each other by an impervious suhstrate film.

18. The backing of claim 1, wherein the foam backing is prepared from a cross-linked ethylene/vinyl acetate copolymer.

* * * * *

UNITED STATES PATENT AND TRADEMARK OFFICE
CERTIFICATE OF CORRECTION

PATENT NO. : 4,554,191

DATED : November 19, 1985

INVENTOR(S) : Korpman

It is certified that error appears in the above-identified patent and that said Letters Patent is hereby corrected as shown below:

Claim 17, line 43, delete "suhstrate" and insert --substrate--.

Signed and Sealed this

Twelfth Day of August 1986

[SEAL]

Attest:

Attesting Officer

DONALD J. QUIGG

Commissioner of Patents and Trademarks